United States Patent
Ruschin et al.

(10) Patent No.: US 9,013,707 B2
(45) Date of Patent: Apr. 21, 2015

(54) DEVICE AND METHOD FOR OPTICAL SENSING OF SUBSTANCES OR ENVIRONMENTAL CONDITIONS

(75) Inventors: Shlomo Ruschin, Herzelia (IL); Tanya Hutter, Beer-Sheva (IL)

(73) Assignee: Ramot At Tel-Aviv University Ltd., Tel-Aviv (IL)

(*) Notice: Subject to any disclaimer, the term of this patent is extended or adjusted under 35 U.S.C. 154(b) by 610 days.

(21) Appl. No.: 13/233,158

(22) Filed: Sep. 15, 2011

(65) Prior Publication Data

US 2012/0013911 A1    Jan. 19, 2012

Related U.S. Application Data

(63) Continuation-in-part of application No. PCT/IB2010/051131, filed on Mar. 16, 2010.

(60) Provisional application No. 61/160,357, filed on Mar. 16, 2009.

(51) Int. Cl.
  *G01B 9/02* (2006.01)
  *G01N 21/77* (2006.01)
  *G01N 33/00* (2006.01)

(52) U.S. Cl.
  CPC ............ *G01N 21/77* (2013.01); *G01N 33/0054* (2013.01); *G01N 2021/7723* (2013.01); *G01N 2021/773* (2013.01); *G01N 2021/7773* (2013.01); *G01N 2021/7783* (2013.01);
  (Continued)

(58) Field of Classification Search
  CPC ......... G01J 3/45; G01J 3/4531; G01J 3/4532; G01J 2003/45; G01B 9/0205; G01B 11/161; G01D 5/35312
  USPC .......................................... 356/451
  See application file for complete search history.

(56) References Cited

U.S. PATENT DOCUMENTS

| 5,929,990 A | * | 7/1999 | Hall ............................. 356/519 |
| 6,016,199 A | * | 1/2000 | Newton ........................ 356/519 |
| 6,897,965 B2 | | 5/2005 | Ghadiri et al. |

(Continued)

OTHER PUBLICATIONS

Janshoff, Macroporous p-Type Silicon Fabry-Perot Layers. Fabrication, Characterization, and Applications in Biosensing, J. Am. Chem. Soc. 1998, 120, 12108-12006.*

(Continued)

*Primary Examiner* — Tarifur Chowdhury
*Assistant Examiner* — Jonathon Cook
(74) *Attorney, Agent, or Firm* — Mark M. Friedman

(57) ABSTRACT

A device for optical sensing of substances or environmental conditions in a fluid includes a number of non-overlapping adjacent sensing elements, each having a layered optical element for generating a wavelength-specific interference effect and being treated so as to respond to the presence of a predefined substance or a predefined environmental condition to cause an optically detectable change. The sensing elements are distinct from each other both in their wavelength-specific interference effect and in the corresponding optically detectable change. As a result, when the device is illuminated by a common illumination beam of multi-wavelength illumination, spectral analysis performed on the reflected or transmitted illumination enables simultaneous sensing of a plurality of substances or environmental conditions. In certain preferred implementations, the layered optical element includes at least one layer of porous silicon.

17 Claims, 8 Drawing Sheets

(52) U.S. Cl.
CPC  *G01N2021/7793* (2013.01); *G01N 2021/7796* (2013.01)

(56) References Cited

U.S. PATENT DOCUMENTS

| | | | | |
|---|---|---|---|---|
| 2005/0254062 | A1* | 11/2005 | Tan et al. | 356/480 |
| 2007/0070347 | A1* | 3/2007 | Scherer et al. | 356/326 |
| 2007/0148760 | A1* | 6/2007 | Klesel et al. | 435/287.2 |

OTHER PUBLICATIONS

Saha, Porous Silicon Sensors—Elusive and Erudite, International Journal on Smart Sensing and Intelligent Systems, vol. 1, No. 1, Mar. 2008.*

Sutapun B et al :"Pd-coated elastooptic fiber optic Bragg grating sensors for multiplexed hydrogen sensing"Sensors and Actuators B 60 1999. 27-34.

Anne M. Ruminski, Matthew M. Moore, and Michael J. Sailor*: "Humidity-Compensating Sensor for Volatile Organic Compounds Using Stacked Porous Silicon Photonic Crystals"Adv. Funct. Mater. 2008, 18, 3418-3426.

Claudia Pacholski,† Marta Sartor,† Michael J. Sailor,*,† Fre'de' rique Cunin,‡ and Gordon M. Miskelly§:"Biosensing Using Porous Silicon Double-Layer Interferometers: Reflective Interferometric Fourier Transform Spectroscopy"J. Am. Chem. Soc. 9 vol. 127, No. 33, 2005 11636-11645.

* cited by examiner

DEVICE AND METHOD FOR OPTICAL SENSING OF SUBSTANCES OR ENVIRONMENTAL CONDITIONS

FIELD AND BACKGROUND OF THE INVENTION

The present invention relates to a device and method for optical sensing of substances or environmental conditions.

As one particular non-limiting application of the present invention, the invention will be exemplified below with reference to applications for sensing ammonia. Ammonia is an extremely important bulk chemical widely used in fertilizers, plastics and explosives, and also implemented as a coolant in large industrial refrigeration systems. On the other hand it is a toxic and flammable gas and therefore needs to be monitored. Ammonia is also listed as one of the marker molecules in breath that could be used to identify diseases like Uremia and kidney impairment.

Various sensors have been proposed for ammonia detection. Many take advantage of the basicity of ammonia by employing a pH sensitive dye. The principle of these sensors is based on the change of color of the detecting molecule immobilized in the optical structure in the presence of gas. Several approaches have been reported for realizing optical ammonia sensors based on pH indicators in fibers, waveguides, or immobilized into porous structures. The detection of ammonia in a humid environment like animal breath is of particular interest. In this reaction, salvation of gaseous ammonia and the pH indicator is required, because the protonation/deprotonation reaction is mediated by water. Moisture is therefore an important factor in this sensing mechanism, since it definitely influences the sensor's reading towards ammonia. In some cases, the response of the sensor towards water vapor may cause cross sensitivity with ammonia, because these two molecules have similar size and volume. Researchers have therefore recognized that water vapor has to be accurately monitored simultaneously with ammonia so these sensors could to be used in practical applications.

U.S. Pat. No. 6,897,965 to Ghadiri et al. discloses an approach for substance detection in which a layer of porous silicon (PSi) is impregnated with an indicator material of which the refractive index changes when it is exposed to the corresponding substance. The change in the refractive index of the layer is detected as a shift in the reflected interference pattern generated by the layer.

In "*Biosensing Using Porous Silicon Double-Layer Interferometers. Reflective Interferometric Fourier Transform Spectroscopy*" (Claudia Pacholski et al., *J. Am. Chem. Soc.*, 2005, 127 (33), 11636-11645) and "*Humidity-Compensating Sensor for Volatile Organic Compounds Using Stacked Porous Silicon Photonic Crystals*" (Anne Ruminski et al., *Adv. Funct. Mater.* 2008, 18, 3418-3426), this approach is expanded to a two-layer structure in which variations in the optical properties of two stacked layers are sensed simultaneously to determine two different variable parameters. As detailed in Pacholski et al., the stacking of two sensing layers considerably complicates the spectral analysis of the output, since each layer individually and the combination of the two layers each generate a corresponding interference pattern in the reflected spectrum. While proposing a solution for the suggested two-layer structure, this approach does not seem to be suitable for generalization to more than two layers.

There is therefore a need for a device which would facilitate simultaneous sensing of a plurality of substances and/or environmental conditions in a fluid by straightforward spectral analysis, and which would facilitate scaling up of the device to sense multiple parameters.

SUMMARY OF THE INVENTION

An embodiment of the present invention is a device and corresponding method for optical sensing of substances or environmental conditions in a fluid.

According to an embodiment of the present invention there is provided, a device for optical sensing of substances or environmental conditions in a fluid, the device comprising: a plurality of non-overlapping adjacent sensing elements, each of the sensing elements comprising a layered optical element for generating a wavelength-specific interference effect, wherein each of the layered optical elements is treated so as to be responsive to presence of a predefined substance or a predefined environmental condition to cause an optically detectable change, and wherein the sensing elements are distinct from each other both in the wavelength-specific interference effect and in the optically detectable change such that, when the device is illuminated by a common illumination beam of multi-wavelength illumination, spectral analysis performed on the reflected or transmitted illumination enables simultaneous sensing of a plurality of substances or environmental conditions.

According to a further feature of an embodiment of the present invention, the layered optical element includes at least one layer of porous silicon.

According to a further feature of an embodiment of the present invention, the sensing elements are distinguished by a thickness of the at least one layer of porous silicon.

According to a further feature of an embodiment of the present invention, at least one of the sensing elements is treated by oxidation of surfaces of the at least one layer of porous silicon.

According to a further feature of an embodiment of the present invention, at least one of the sensing elements is treated by association of an indicator with the sensing element.

According to a further feature of an embodiment of the present invention, the indicator is a primary structural component of at least one layer of the layered optical element.

According to a further feature of an embodiment of the present invention, the indicator of at least one of the sensing elements comprises a temperature responsive material.

According to a further feature of an embodiment of the present invention, the indicator of at least one of the sensing elements comprises a pressure responsive material.

According to a further feature of an embodiment of the present invention, the indicator of at least one of the sensing elements is responsive to presence of the predefined substance or the predefined environmental condition to undergo a color change in absorption spectrum.

According to a further feature of an embodiment of the present invention, the indicator of at least one of the sensing elements is responsive to presence of the predefined substance or the predefined environmental condition to undergo a change in refractive index.

According to a further feature of an embodiment of the present invention, the indicator of at least one of the sensing elements is responsive to presence of the predefined substance or the predefined environmental condition to undergo a change in dimensions.

According to a further feature of an embodiment of the present invention, the indicator of at least one of the sensing elements comprises at least one of the group consisting of: pH sensitive dyes, porphyrins, metalloporphyrins, proteins, antibodies and DNA.

According to a further feature of an embodiment of the present invention, the plurality of sensing elements includes at least three sensing elements.

According to a further feature of an embodiment of the present invention, the plurality of sensing elements includes at least four sensing elements.

According to a further feature of an embodiment of the present invention, there is also provided a reference element arranged in non-overlapping relation adjacent to the plurality of sensing elements, the reference elements comprising a layered optical element for generating a wavelength-specific interference effect distinct from the wavelength-specific interference effect of each of the sensing elements, the reference element being provided without an indicator so as to provide a calibration reference when illuminated together with the sensing elements.

According to a further feature of an embodiment of the present invention, the plurality of sensing elements are integrated onto a common semiconductor chip.

According to a further feature of an embodiment of the present invention, there is also provided an illumination arrangement directing multi-wavelength light simultaneously towards all of the reference elements.

According to a further feature of an embodiment of the present invention, there is also provided a spectral analysis arrangement deployed to receive and separate the spectral components of light reflected from or transmitted through the sensing elements, thereby identifying the spectral features corresponding to each sensing and/or reference element, and detecting changes in those spectral features indicative of the state of the indicator of each sensor element.

According to a further feature of an embodiment of the present invention, the plurality of sensing elements are mounted in fixed spatial relation to an end of an optical waveguide in such a manner that the plurality of sensing elements are simultaneously illuminated by illuminating radiation propagating along the optical waveguide and radiation reflected from the sensing elements returns along the optical waveguide.

According to a further feature of an embodiment of the present invention, the optical waveguide is an optical fiber, and wherein the plurality of sensing elements are attached to a terminal surface of the optical fiber.

There is also provided according to an embodiment of the present invention, a method for sensing substances or environmental conditions in a fluid comprising: (a) providing the device defined above; (b) directing multi-wavelength light simultaneously towards all of the reference elements; and (c) separating the spectral components of light reflected from or transmitted through the sensing elements, thereby identifying the spectral features corresponding to each sensing and/or reference element, and detecting changes in those spectral features indicative of the state of the indicator of each sensor element.

BRIEF DESCRIPTION OF THE DRAWINGS

Certain embodiments of the invention are herein described, by way of example only, with reference to the accompanying drawings, wherein.

DESCRIPTION OF THE PREFERRED EMBODIMENTS

An embodiment of the present invention is a device and corresponding method for simultaneous optical sensing of several substances or environmental conditions in a fluid.

The principles and operation of devices and methods according to the present invention may be better understood with reference to the drawings and the accompanying description.

Overview

Figure 1A:
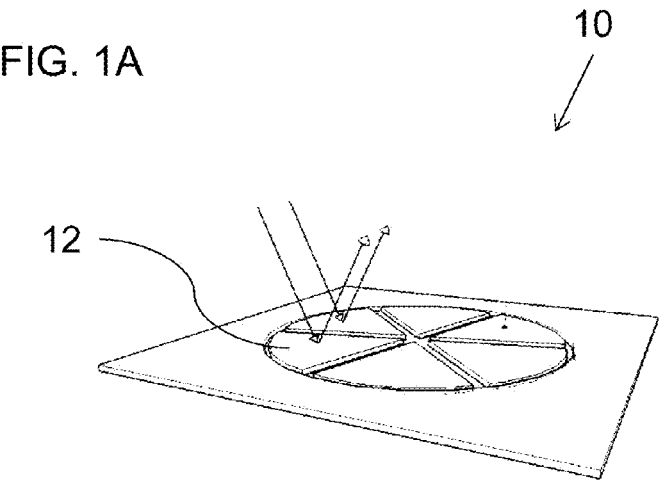
FIG. 1A is a schematic representation of a device, constructed and operative according to an embodiment of the present invention, for simultaneous optical sensing of several substances or environmental conditions in a fluid.

Referring now to the drawings, FIG. 1A illustrates schematically a device, generally designated 10, constructed and operative according to the teachings of an embodiment of the present invention, for simultaneous optical sensing of several substances or environmental conditions in a fluid ((liquid or gas phase). Device 10 preferably includes a plurality of non-overlapping adjacent sensing elements 12. Each sensing element 12 typically includes a layered optical element for generating a wavelength-specific interference effect. Each sensing element is treated, such as by provision of an indicator associated with the layered optical element, so as to be responsive to presence of a predefined substance or a predefined environmental condition to cause an optically detectable change. According to one particularly preferred set of non-limiting implementations, sensing elements 12 are implemented as regions of porous silicon (PSi), and an indicator is impregnated within the pores of the PSi. Each of the sensing elements is preferably distinct from all others of the sensing element, both in the wavelength-specific interference effect and in the optically detectable change, such that, when the device is illuminated by a common illumination beam of multi-wavelength illumination, spectral analysis performed on the reflected or transmitted illumination enables simultaneous sensing of a plurality of substances.

Thus, in an example, device 10 essentially functions as a sensor array in which each section is made of porous silicon with a different functionality, such as a different immobilized indicator dye. By way of example, in each sample, the PSi film may differ in thickness and/or porosity, so that the thin-film reflection spectrum of each of the array components varies in periodicity. This periodicity distinction effectively encodes the spectrum in such a way that the distinct variations can be analyzed using spectral data analysis methods.

Figure 2:
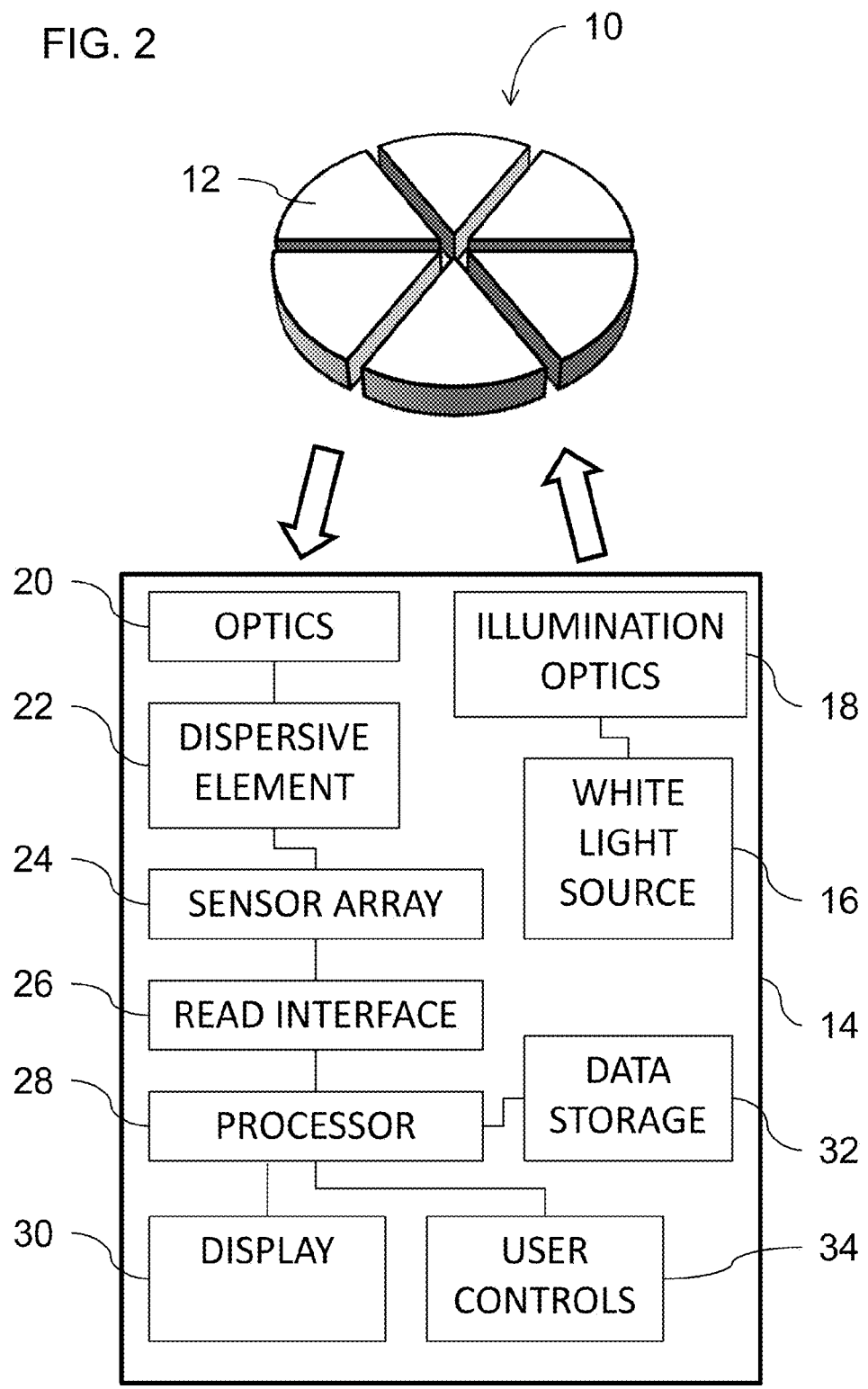
FIG. 2 is a block diagram showing a system for performing measurement of parameters sensed by the device of FIG. 1A.

FIG. 2 shows schematically an exemplary non-limiting implementation of an interrogation device, generally designated 14, for reading device 10. Reading of the device may be performed by collimating white light from white light source 16 via illumination optics 18 to illuminate all of sensing elements 12 at once. Light reflected from the sensing elements is collected by receiving optics 20 and conveyed, typically via a single fiber, to a spectrometer, represented here schematically by dispersive element 22, sensor array 24 and read interface 26. Since no imaging is implemented in the light collection, the obtained spectrum consists of many overlapping interference spectra each reflected from a different sensing element. In order to separate the information regarding each sensing element, the sensed data is processed by a processor 28, applying a FFT algorithm to the combined spectrum.

Figure 1B:
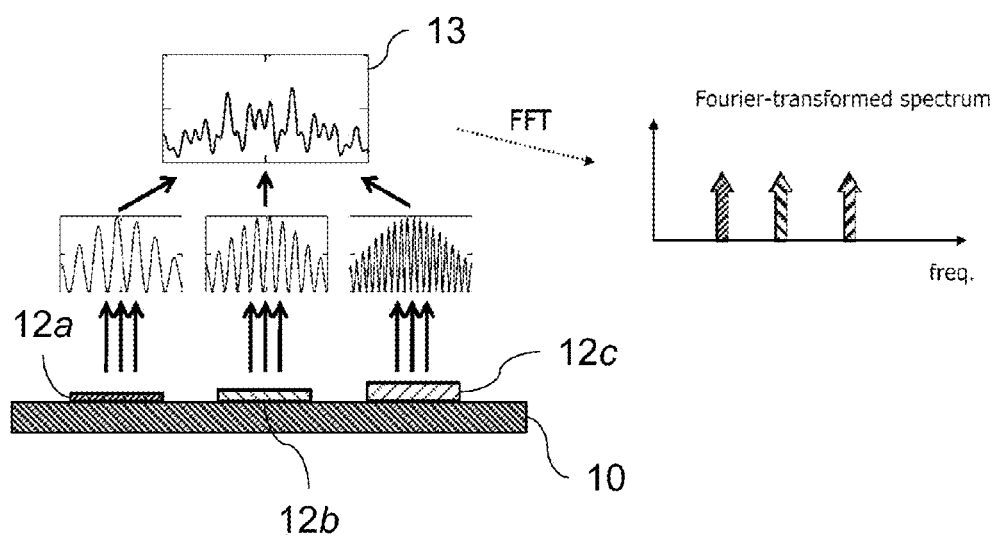
FIG. 1B is a schematic illustration of a principle of spectral encoding employed according to an embodiment of the present invention.

FIG. 1B illustrates schematically the principles underlying the spectral encoding approach exemplified herein. Specifically, three different sensing regions, labeled 12*a*, 12*b* and 12*c*, respectively, are implemented as layers of differing thicknesses, giving rise to reflected interference patterns with correspondingly different characteristic frequency variation patterns. The overall reflected spectral response is illustrated at 13. By processing this spectrum by Fourier transform, a peak corresponding to each sensing element can be clearly distinguished. Variations in the amplitude, shape or position of this peak can then be used to track variations in optical properties of an indicator or other optical variables associated with the corresponding sensor element. It is preferably that peaks in the Fourier-transformed spectrum for each porous silicon sensor will be spread apart to allow good material discrimination. The location of the peak depends on the refractive index (porosity) and the thickness of the layers, and these parameters are easily controlled in the electro-chemical processing of porous silicon, as is known in the art.

Definitions

Before addressing the features of certain implementations of the present invention in more detail, it will be helpful to define certain terminology as used herein in the description and claims. Firstly, where reference is made to an element "treated so as to be responsive to presence of a predefined substance or a predefined environmental condition to cause an optically detectable change", this refers to any treatment, whether by chemical or physical processing of the optical layered structure itself or by addition thereto of a supplementary material to imbue the structure with the required variable optical properties. The optically detectable change is not necessarily sufficient to provide direct data regarding the substance or environmental condition, and may need to be combined with additional data, for example, measurements of other interrelated parameters by other sensing elements, as will be exemplified below with reference to the ammonia sensor example. The response to the presence of a substance or parameter may be a binary (e.g., threshold) response, or may be a continuous (quantitative) response.

The phrase "predefined substance or predefined environmental condition" encompasses all sorts of chemical and physical conditions including, but not limited to, presence of a given element, compound or combination of compounds, more general chemical conditions, such as pH, oxidizing or reducing conditions, and physical parameters such as temperature, pressure, ionizing or non-ionizing radiation of various types.

Where reference is made to "at least two predefined substances or predefined environmental conditions", this refers to at least two all together, i.e., at least two substances only, at least two environmental conditions only, or at least one substance and at least one environmental condition. "At least three" or any other number should also be interpreted similarly.

When referring to the sensor elements as being "adjacent", this refers to elements sufficiently close to facilitate simultaneous illumination with an interrogation light beam. The sensor elements are most preferably located in a close packed arrangement with each sensor element within about 10% of its own maximum dimension from its neighboring sensor elements.

The term "non-overlapping" is used here to refer to elements of which the surface can be illuminated directly at the same time without the illuminating beam passing through another of the sensing elements, in contrast to the stacked sensor structures of Pacholski and Ruminski mentioned above.

The term "layered optical element" in this context is used to refer to any structure having one or more layer disposed thereon, either as a uniform layer or with internal structure, so as to generate a wavelength-specific interference effect. In some cases, a multi-layer structure may be used, made up of many layers each with slightly different optical and/or chemical properties. "Wavelength-specific" in this context refers to any optical response which has distinctive wavelength dependence at one or more specific wavelengths or wavelength bands.

Various preferred implementations of the reading arrangement for use in the present invention are referred to as "non-imaging" in the sense that dispersive element 22 receives simultaneously light reflected or transmitted by more than one sensing element 12.

Device Structure

Turning now to the features of an embodiment of device 10 in more detail, as mentioned above, in certain preferred embodiments, at least one of the layered optical element includes at least one layer of porous silicon. The different sensing elements are preferably distinguished by a thickness of the at least one layer of porous silicon. The use of porous silicon allows deployment of an indicator material at least partially within pores of the layer of porous silicon. In certain preferred examples, each sensing element includes at least one layer of thickness between 0.2 and 10 microns.

The optically detectable change occurring in the sensing elements 12 may be one or more of a number of different types of change. Examples include, but are not limited to, a change in the absorption spectrum (within or beyond the visible range), a change in refractive index, and a change in layer thickness.

In certain preferred embodiments, the indicator of at least one of the sensing elements includes a temperature responsive material. Examples of temperature responsive materials include thermochromic materials, such as:

Cresol red dye [A. Seeboth et. al., *J. Mater. Chem.*, vol. 9, pp. 2277-2278, 1999]

Betaine dye 2,6-diphenyl-4-(2,4,6-triphenylpyridinio) phenolate [A. Seeboth et. al., *J. Mater. Chem.*, vol. 9, pp. 2277-2278, 1999]

Reichardt's dye [M. C. Burt and B. C. Dave, *Sensors and Actuators* B 107, 552-556, 2005]

spiroxazine 7 [S. H. Kim et. al. *Dyes and Pigments*, 53, 251-256, 2002]

In certain preferred embodiments, the indicator of at least one of the sensing elements includes a pressure responsive material. Examples of such materials include barochromic materials such as:

Betaine dye 3 [C. Reichardt et. al., *Pure & Appl. Chem.*, vol. 65, no. 12, pp. 2593-2601, 1993]

poly(thiophenes) [Leclerc, *Advanced Materials*, 11, 18, 1491-1498, 1999]

poly(alkyl silanes) [Song et al, *Macromolecules*, 25, 3629-3632, 1992]

pentacyanoferrates (II) [S. Alshehri at. Al., Transition Metal Chemistry, Vol. 18, no. 6, 1993]

In certain preferred embodiments, an indicator associated with at least one of the sensing elements is responsive to presence of the predefined substance or the predefined environmental condition to undergo a change in spectral response. This may express itself as a color change, or as any other change in the relative intensities of wavelengths in absorbed, reflected or transmitted light, whether visible or non-visible.

In certain preferred embodiments, an indicator associated with at least one of the sensing elements is responsive to presence of the predefined substance or the predefined environmental condition to undergo a change in refractive index.

In certain preferred embodiments, an indicator associated with at least one of the sensing elements is responsive to presence of the predefined substance or the predefined environmental condition to undergo a change in dimensions. Examples of such materials include materials which swell, thereby changing the layer thickness, such as:

poly(ethylene-vinyl acetate) [T. J. Plum, IEEE Explore, 2006]

pH-sensitive hydrogel [M. Lei et. al., In: 17th IEEE MEMS Conference. Maastricht, The Netherlands: IEEE MEMS, 2004:391-394]

PBA hydrogels [Y. Gu and R. A. Siegel, In: 28th International Symposium on Controlled Release of Bioactive Materials, San Diego, Calif. Minneapolis, Minn.: The Controlled Release Society, 2001

In certain preferred embodiments, an indicator associated with at least one of the sensing elements comprises at least one of the group consisting of: pH sensitive dyes, porphyrins, metalloporphyrins, proteins, anti-bodies and DNA.

As mentioned earlier, one particular advantage of the side-by-side deployment of the sensing elements is that the device can be scaled to include three, four or more sensing elements. In the schematic example of FIGS. 1 and 2, device 10 is illustrated with six distinct sensing elements 12.

Optionally, in addition to, or in place of, one of sensing elements 12, there is provided a reference element arranged in non-overlapping relation adjacent to the of sensing elements. The reference element comprising a layered optical element for generating a wavelength-specific interference effect distinct from the wavelength-specific interference effect of each of the sensing elements, but without any indicator. This provides a calibration reference when illuminated together with the sensing elements, facilitating elimination of any errors which may be caused by variations in illumination intensity or any other variations not related to the sensor reading process.

In certain preferred embodiments, the plurality of sensing elements are integrated onto a common semiconductor chip. The device may thus optionally be incorporated as part of a "lab on chip" device, for example, where circuitry which constitutes at least part of the sensor reading arrangement is integrated with the sensing elements on a single chip.

Sensor Reading Arrangement

For reading the output of the device, an illumination arrangement is used to direct multi-wavelength light (for example, white light) simultaneously towards all of the reference elements. A spectral analysis arrangement is deployed to receive and separate the spectral components of light reflected from or transmitted through said sensing elements, thereby identifying the spectral features corresponding to each sensing and/or reference element, and detecting changes in those spectral features indicative of the state of the indicator of each sensor element.

An exemplary implementation of an interrogation device 14 for reading device 10 is shown in FIG. 2, and was at least partially described above. The illumination arrangement and spectral analysis arrangement of interrogation device 14 may be integrated with the sensing device 10 described herein to form a free-standing self-contained sensing device. Alternatively, interrogation device 14 may be a separate "reader" unit, optionally a portable unit, which can be aligned to read each of a plurality of different sensing devices.

Depending on the chosen application and type of implementation of the system, device 14 typically has various additional features. A data storage device 32 typically stores various data needed for deriving and interpreting the reading from the sensor, which may include calibration data for the sensor, look-up tables or a parametric model for determining the output of the sensor. Further details of the required processing to derive output readings from the sensed spectral data will be clear to one ordinarily skilled in the art on the basis of the detailed description of the specific example of a combined ammonia and humidity sensing device described below.

Data storage device 32 may also store the sensor outputs, for later retrieval. A display 30 is typically provided to provide immediate feedback to the operator as to the sensor outputs, and user controls 34 may be provided to actuate the sensor and define any user-defined settings. It will be clear that the input and output features are not exclusive of other options which also fall within the scope of this disclosure, such as, for example, a remotely operated sensor with wired or wireless communication but without any local display or user controls.

Although the interrogation arrangement has been described herein with reference to a particularly preferred implementation using white light illumination and spectral analysis, other sensor reading modalities may also be used within the scope of the present invention. For example, in some cases, reading of the sensor may be performed using a tunable monochromatic illumination source stepping or scanning through a given wavelength range of relevance for sensing the output of device 10. Although this approach greatly increases the complexity of the illumination arrangement required, this may be compensated for by the simplicity of the optical monitoring arrangement which does not require spectral analysis.

Optical Fiber-Based Implementations

One subset of implementations of the present invention employs sensing regions deployed in fixed relation to the tip of an optical waveguide, such as an optical fiber, which are interrogated by illuminating radiation propagating along the waveguide and reflected from the sensing regions back along the waveguide. This configuration is particularly suitable for use as a probe for positioning at a desired location, or for introduction into a body (e.g., during endoscopy or other minimally invasive surgical techniques).

Figure 12:
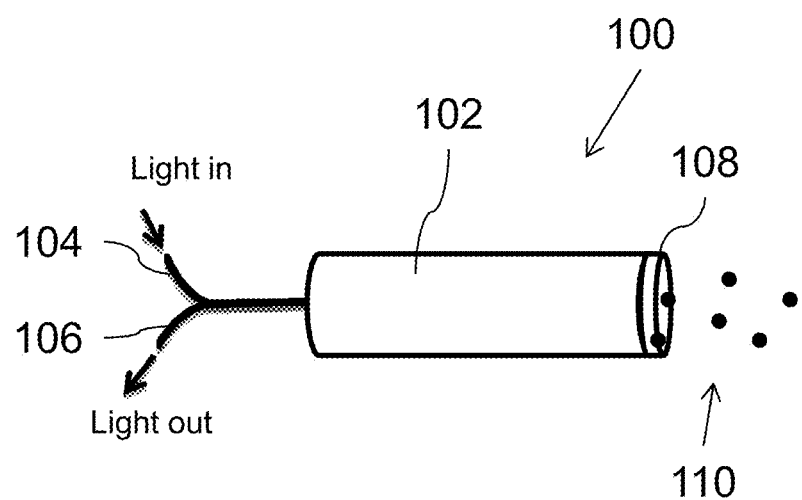
FIG. 12 is a schematic representation of an optical fiber-based implementation of a device, constructed and operative according to an embodiment of the present invention, for simultaneous optical sensing of several substances or environmental conditions in a fluid.
Figure 13:
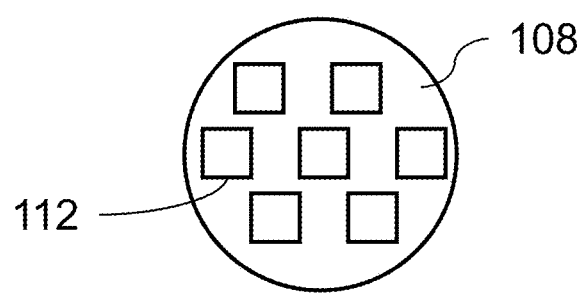
FIG. 13 is a schematic enlarged end view of a fiber probe from the device of FIG. 12.

An exemplary optical waveguide implementation is illustrated in FIGS. 12 and 13. Specifically, FIG. 12 shows a device, generally designated 100, constructed and operative according to an embodiment of the present invention, having a multi-mode sensor fiber 102 which is fed by light introduced along an input fiber 104 from an illumination arrangement (e.g., white light source 16 via illumination optics 18 described above, not shown here) and feeds at least part of the returned radiation via an output fiber 106 to an analysis arrangement (e.g., a detector or spectrometer as described above, not shown here). Sensor fiber 102 is preferably a multi-mode fiber having a core typically with a diameter in the range of 50 to 500 microns. A large diameter single-mode fiber may also be used. A thin film sensor 108 is attached to a cleaved end of optical fiber 102. As best seen in FIG. 13, sensor 108 has a plurality of sensing elements 112, analogous to sensing elements 12 described above, which are placed in non-overlapping relation over the end surface of the fiber. Suitable technology for manufacture of sensing elements of suitable dimensions for combining on the end of a fiber of the dimensions mentioned are commercially available. One example of suitable technology is documented in the article "Biomolecular screening with encoded porous-silicon photonic crystals", F. Cunin et al., Nature Materials, Vol. 1, September 2002, pp. 39-41, which presents micrometer-sized optically encoded porous silicon particles. Adjacent sensing pads with differing properties can be produced by selective etching or deposition processes performed while others of the pads are protected by appropriate masks. Optionally, if it is desired to use larger area sensing elements, a beam expander or collimating lens may be interposed between the tip of the fiber and the sensing elements, spreading the beam to, for example, a diameter of 1-3 millimeters. The effectively provides an enlarged terminal surface to the optical fiber, to which the sensing elements may be directly attached. Where adhesives are used to fasten the sensing elements to the terminal surface, various epoxy adhesives have suitable optical properties, such as adhesives commercially available from Norland Products Inc., N.J. (USA).

It will be noted that the sensing elements in this configuration are typically illuminated from the side opposite the exposed surface at which linking with the detected molecules occurs. Rear illumination of this sort can be used effectively so long as the interrogating light beam reaches the front interface where the linking takes place. If a substrate or support film is used behind the sensing elements, the substrate should be transparent to the wavelengths used.

In use, light is fed into sensing fiber 102 via input fiber 104, and light reflected by the sensing elements 112 is transmitted back via output fiber 106 to a detector or spectrometer. As before, the different sensing elements 112 are produced with differing spectral reflection properties, and with sensitivity to different analytes or environmental properties, allowing simultaneous interrogation and resolution of measurements for different parameters, such as the concentration of analyte molecules 110 in the proximity of the probe tip, all as detailed above.

In order to illustrate more fully the principles of certain embodiments of the present invention, and to exemplify aspects of a practical implementation thereof, there will now be presented a particular example relating to sensing of ammonia and humidity in gas. From the details of this example, one ordinarily skilled in the art will readily understand how to implement a wide range of other applications.

Example I

Ammonia Sensor

Overview

Figure 3A:
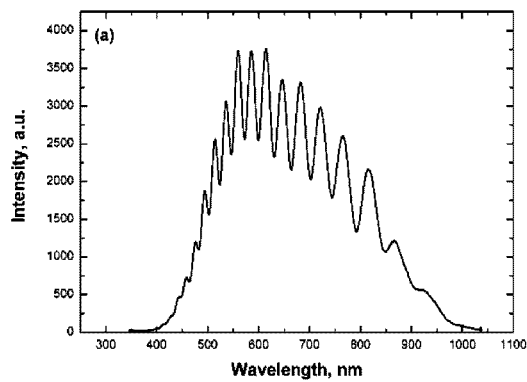
FIGS. 3A-3C are reflectance spectra from a first sensing element, from a second sensing element and combined from the two sensing elements, respectively, for an exemplary implementation of a simplified two-element device similar to that of FIG. 1A employing immobilized pH indicator porous silicon and oxidized porous silicon.
Figure 3B:
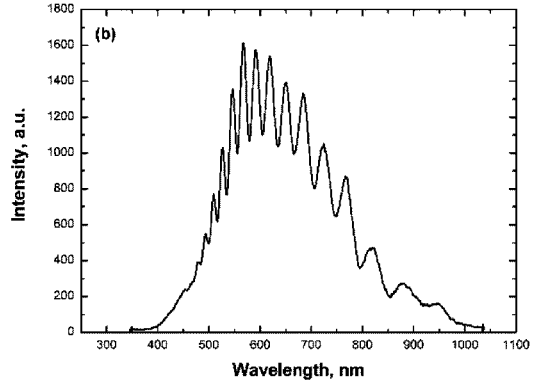

A two-sensor-element device was fabricated in which the sample was sectioned into two parts: one for water vapor and one for ammonia. Correspondingly, one half was made of oxidized porous silicon and the other one was made of porous silicon with a chemical pH indicator dye immobilized inside the pores. As demonstrated below, the oxidized half is reversibly highly sensitive towards water vapor, and therefore used as a humidity sensor. Humidity sensors based on porous silicon already have been reported in the literature (for example, in C. J. Oton et al. "Multiparametric porous silicon gas sensors with improved quality and sensitivity," *Phys. Stat. Sol.* (*a*), vol. 197, no. 2, pp. 523-527, May 2003). The pH indicator dye which was immobilized into the second half, responds to both ammonia concentration and humidity. The combined use of both sensors enables the separate determination of these two components. The reflection spectrum for each half is presented in FIGS. 3A and 3B, and the combined spectrum reflected from both samples is shown in FIG. 3C.

Figure 3C:
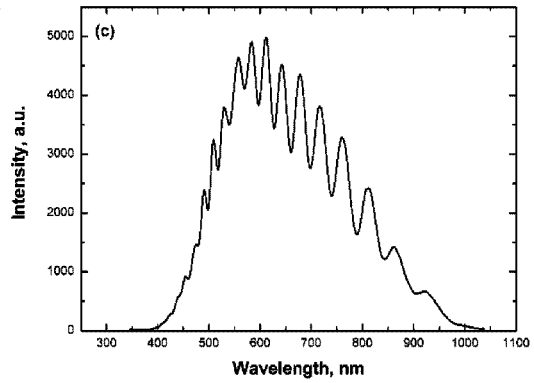

As seen in FIG. 3C, the combined spectral graph received from a single white beam, does not allow the discrimination of the signals arriving from each half, since we work under non-imaging conditions. Observing FIGS. 3A and 3B, it is apparent that the sinusoidal shapes in both graphs have a quasi-periodical appearance. As known, the ideal response of the reflectivity of a single thin film is periodic in $(1/\lambda)$ with subsequent peaks distanced by:

$$\frac{1}{\lambda_m} - \frac{1}{\lambda_{m+1}} = \frac{1}{2 \cdot n \cdot d} \quad (1)$$

where d is the thickness of the film and n is its refractive index. Both parameters can be determined originally in the PSi layer etching process. The sensing process may affect both the refractive index and the absorption coefficient of the sensing layer.

Measurements, calibration and analysis of data were performed according to the following sequence: As a first step for each set of measurements, the reflected reference spectrum (measured in dry nitrogen only) was subtracted from all the measured spectra. In the next step, the x-coordinate of reflected spectra was inverted from wavelength (nm) to wavenumbers ($nm^{-1}$) and a linear interpolation was applied in order to obtain an evenly spaced new x-axis. Finally a FFT algorithm was applied. Each porous silicon section produces a characteristic peak in the Fourier domain. The position of the peak depends on the porous layer properties, and therefore is unique for each set of fringes. In our case we apply FFT on the difference spectra (and not the absolute), thus when water vapor is introduced into the system, a red-shift of the oxidized half spectrum is observed, causing peaks to occur in the Fourier domain at the original periodicity value. The more water condenses in the pores, the bigger the amplitude of the difference graph, and the higher the peak seen in the "frequency domain". When dry ammonia is introduced, there is absorbance at 550-650 nm, and an additional peak at low frequencies (F~0-1) occurs. Thus, the absorbance of ammonia also affects the Fourier spectrum but at different spectral ranges and in a differential manner as will be shown below.

Experimental Setup

The experimental procedure was as follows. All samples were prepared using p-type doped Si substrates, 405-645 µm thick with a resistivity of 0.01-0.02 Ω-cm and (100) crystal orientation. The silicon wafer was diced into 1 $cm^2$ chips, and each chip was electrochemically etched using an electrolyte solution containing 30% HF (48% aqueous) and 70% ethanol. Porous layers of 3 and 5 µm were etched with a current density of 50 mA/$cm^2$ for 86 s and 143 s respectively Immediately after etching, each chip was rinsed with ethanol and then with pentane.

Indicator solutions were prepared by dissolving 100 mg pH indicator dye Bromotymol blue (BTB) in 30 mL ethanol. A volume of 15 µL dye solution was deposited on the surface of one sample, and the sample was left to dry for 24 hours.

Thermal oxidation was carried out in air on another sample at 300° C. for 30 min, and then heated further to 900° C. for another 30 min. Thermal pre-oxidation at 300° C. is known to have a stabilizing effect on PSi by hindering the fragile texture of the material from collapsing during further treatments at higher temperatures. Thermal oxidation increases the hydrophilicity of the porous layer, allowing water vapor to effectively infiltrate the pores.

Experiments were performed using synthetic ammonia gas in nitrogen. Further dilution of ammonia gas with nitrogen was achieved through the use of mass flow controllers. Humid $N_2$ was obtained by allowing the dry $N_2$ to bubble through a container of distilled water which provided a relative humidity (RH) of 100%. This flow was further diluted with a second flow of pure nitrogen or the $NH_3$ in nitrogen mixture before reaching the sample. By changing the relative flow rates, it was possible to achieve different concentrations of water vapor/ammonia.

The sensor was placed into a sealed flow cell with a quartz window to enable light illumination of the sensor. Light from a tungsten halogen lamp was transmitted through six 400 µm fibers and used as the illumination source. Reflected light was collected by a fiber located in the middle of the bundle.

In order to investigate the spectral changes in each sample individually during the experiments, a special beam arrangement was constructed employing a cube beam-splitter and a prism (not shown), making it possible to observe the combined spectrum, as well as each separate spectrum by covering one of the beams. This setup was used for experimental evaluation only. A practical device preferably employs a single white-light beam and measures the combined reflected light. The reflection spectrum was measured over a spectral range 500-1000 nm, using a compact spectrometer.

Results and Analysis

As mentioned above, the splitter/prism arrangement was designed to allow separate measurement for each section and for their combination. For the purpose of the experiment, this allowed verification that the spectral information from the separated sections can successfully be retrieved from the combined spectrum. We refer first to preliminary measurements taken from each sensor independently.

Figure 4A:
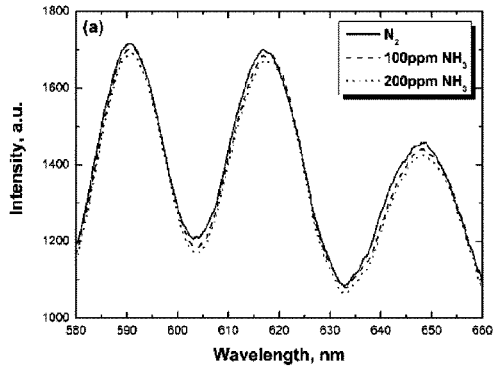
FIGS. 4A and 4B are reflectance spectra from immobilized pH indicator porous silicon and from oxidized porous silicon, respectively, each showing the spectrum received at 0, 100 and 200 ppm ammonia.
Figure 4B:
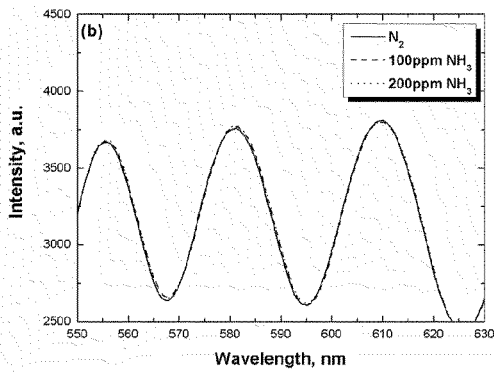

When dry ammonia is present, changes are observed in the pH indicator immobilized porous silicon section only. The oxidized half is not affected in this case, as can be seen in FIGS. 4A and 4B. FIG. 4A indicates that the porous silicon with immobilized pH indicator shows both absorption and a slight sinusoidal shift towards longer wavelengths as a result of addition dry ammonia. This response is also non-linear. FIG. 4B shows that the oxidized porous silicon is inert to dry ammonia. Dry ammonia certainly penetrates the pores, but it doesn't change significantly the effective refractive index of PSi, since the refractive index of gaseous ammonia is similar to that of air. Furthermore the results here were recorded at very low $NH_3$ concentrations. We conclude therefore that oxidized PSi without pH indicator is not affected by ammonia at low concentrations. This conclusion is also supported by the resolved Fourier analysis shown below.

Figure 5A:
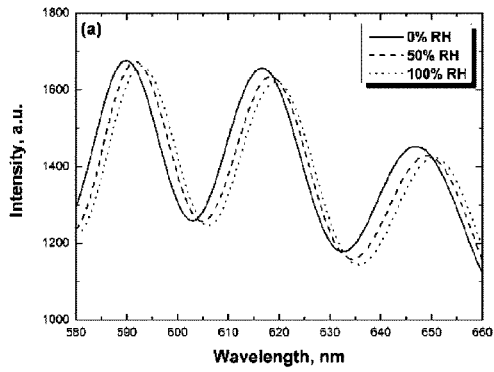
FIGS. 5A and 5B are reflectance spectra from immobilized pH indicator porous silicon and from oxidized porous silicon, respectively, each showing the spectrum received at 0%, 50% and 100% relative humidity.
Figure 5B:
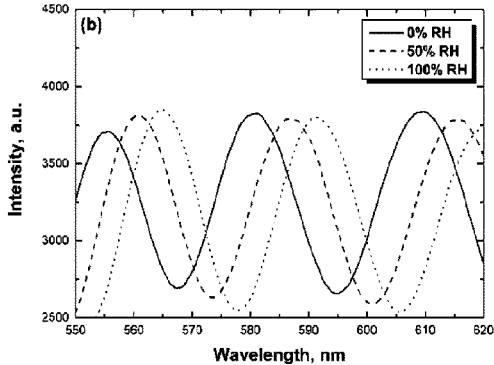

When water vapor is present, the humidity causes a red shift in both samples, (FIGS. 5A and 5B, respectively). As seen here, the oxidized half shows higher affinity towards water vapor. This effect of moisture on the PSi with the pH indicator nevertheless renders the absolute measurement of ammonia concentration non-trivial. This problem is addressed below.

Figure 6:
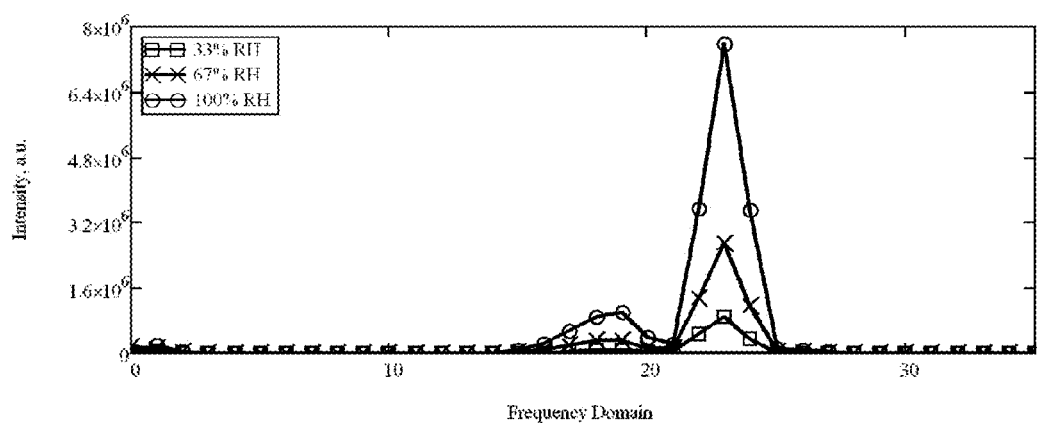
FIG. 6 is a graph showing the FFT of the combined spectrum at three different levels of relative humidity.

FIG. 6 presents variations in the spectral response of the porous structures to pure water vapor. Specifically, measurements were performed at 33%, 67% and 100% relative humidity, at room temperature (25° C.). All spectra were normalized with respect to that of dry nitrogen, while the total flow rate was kept constant at 150 standard cubic centimeters per minute (sccm). FIG. 6 shows the FFT of the combined normalized spectra, exhibiting two peaks, one corresponding to dye immobilized PSi and the other to oxidized PSi. As seen, the peak resulting from the oxidized PSi displays more significant changes, because of its hydrophilicity as compared to the non-oxidized PSi.

The intensity of the peak increases with relative humidity level. Without in any way limiting the present invention, this is believed to be due to the fact that the spectrum on which FFT is applied is not an absolute spectrum but a normalized spectrum. Therefore, slight changes in periodicity appear as peaks in the FFT graph. The more water vapor infiltrates the pores, the bigger the red shift, the bigger the amplitude of the normalized spectrum and therefore the higher the peak.

Figure 7:
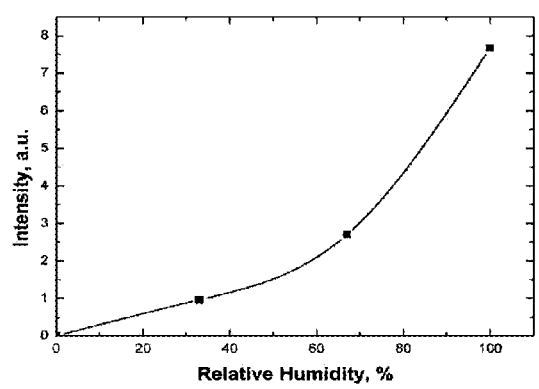
FIG. 7 is a graph showing the intensity of the right-hand peak of FIG. 6, corresponding to the oxidized PSi sensor section, as a function of relative humidity.

FIG. 7 represents the increase in intensity of the peak at F=23 point on the x-axis with the increase in the relative humidity.

Figure 8:
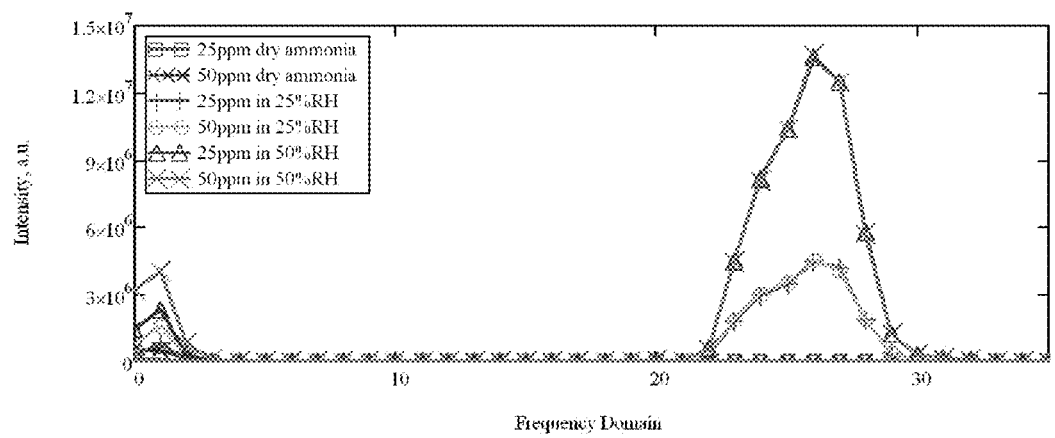
FIG. 8 is a graph showing the FFT of a combined spectrum for 25 and 50 ppm ammonia at 0%, 25% and 50% relative humidity.
Figure 9:
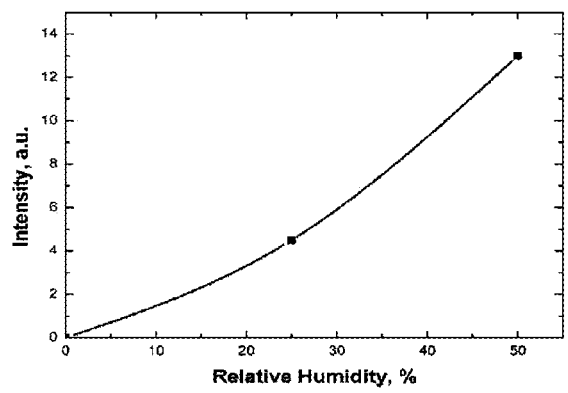
FIG. 9 is a graph showing the intensity of the right-hand peak of FIG. 8, corresponding to the humidity response of the sensor elements, as a function of relative humidity (measured at 0%, 25% and 50%)

Turning now to the combined spectral measurements from the device as a whole, measurements were performed with 25 ppm and 50 ppm of ammonia at 0%, 25% and 50% relative humidity. In this case both PSi sensors were 5 µm thick, with 62% porosity and thermally oxidized. One of them was immobilized with indicator dye. The FFT of the combined spectrum shows two peaks, as presented in FIG. 8. In this case the peak at F=26 (in the x-axis) reflects humidity, and the peak at F=1 reflects absorption induced by ammonia. This sample processing as seen allows practically total differentiation between the humidity and ammonia effects. Thermal oxidation was implemented here in both samples since they are more stable chemically as compared to non-oxidized or partially oxidized samples. In the wavelength domain, the F=1 reflects the appearance of an absorption band due to color change in the dye, while the F=26 position reflects the effect of a change in refractive index of the PSi film.

Following the intensity of the humidity peak, one can conclude about the level of relative humidity in the system (FIG.

Figure 10:
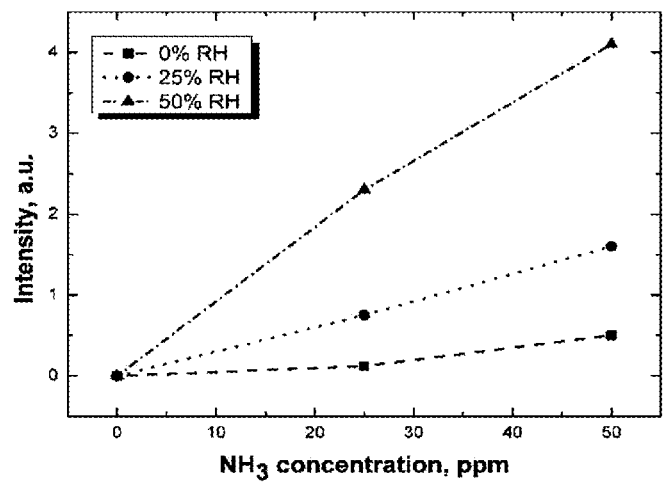
FIG. 10 is a graph showing the intensity of the left-hand peak of FIG. 8, corresponding to ammonia response of the pH indicator sensor section, as a function of ammonia concentration, shown for three levels of relative humidity (0%, 25% and 50%)

9). Then by looking at the intensity of the ammonia peak one can conclude the ammonia concentration, (FIG. 10). As expected, the device's sensitivity towards ammonia is highly dependent on the water vapor content in the gas mixture.

Example II

Low Concentration Sensing

Figure 11:
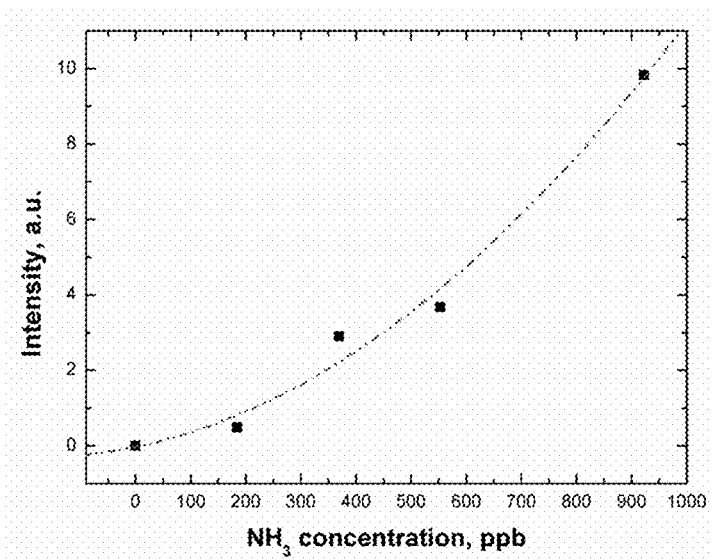
FIG. 11 is a graph showing the intensity of an ammonia-related peak from another example using low ammonia concentrations in a range relevant for breath testing.

In order to demonstrate the relevance of the sensor presented here as a breath ammonia analyzer, measurements were performed at low ammonia concentrations, closer to ammonia concentrations in human breath. For that purpose, a PSi sensor with 3.5 µm thickness and 70% porosity was fabricated, and then thermally oxidized and immobilized with a BCP indicator dye. The measurements were performed at dry conditions at ammonia concentrations ranging from 180 to 922 ppb. The FFT algorithm was applied on the reflected spectrum in the same manner as described previously. The peak at 1 nm (inverse frequency normalized units), which corresponds to the absorption due to ammonia, was recorded as a function of ammonia concentration, and the plot presented in FIG. 11.

The sensitivity was mainly limited by the light source long term instability which may be improved by better current stabilization. Further improvement may be achieved by using a more sensitive indicator dye or by optimizing the concentration and the sensitization method.

It will be appreciated that the above descriptions are intended only to serve as examples, and that many other embodiments are possible within the scope of the present invention as defined in the appended claims.

What is claimed is:

1. A system for optical sensing of substances or environmental conditions in a fluid, the system comprising:
   (a) a sensor device comprising:
      a plurality of non-overlapping adjacent sensing elements, each of said sensing elements comprising a layered optical element for generating a wavelength-specific interference effect,
      wherein each of said layered optical elements is configured to be responsive to presence of a predefined substance or a predefined environmental condition to cause an optically detectable change;
   (b) an illumination arrangement directing multi-wavelength light simultaneously towards all of said sensing elements; and
   (c) a spectral analysis arrangement including receiving optics deployed to combine light reflected from or transmitted through said plurality of sensing elements, and to direct said combined light into a non-imaging spectral analysis subsystem,
      wherein said sensing elements are distinct from each other in the wavelength-specific interference effect such that each of said sensing elements generates characteristic spectral features, said sensing elements being further distinct from each other in said optically detectable change,
      and wherein said spectral analysis arrangement is configured to perform spectral data analysis on the combined reflected or transmitted illumination to identify said characteristic spectral features corresponding to the wavelength-specific interference effect of each sensing element, and to detect changes in those spectral features indicative of the presence of the predefined substance or the predefined environmental condition sensed by each sensor element, thereby achieving simultaneous sensing of a plurality of substances or environmental conditions.

2. The system of claim 1, wherein said layered optical element includes at least one layer of porous silicon.

3. The system of claim 2, wherein said sensing elements differ in a thickness of said at least one layer of porous silicon.

4. The system of claim 2, wherein at least one of said sensing elements has oxidized surfaces in said at least one layer of porous silicon.

5. The system of claim 1, wherein at least one of said sensing elements has an indicator associated with said sensing element.

6. The system of claim 5, wherein said indicator of at least one of said sensing elements comprises a material selected from the group consisting of: a temperature responsive material and a pressure responsive material.

7. The system of claim 5, wherein said indicator of at least one of said sensing elements is responsive to presence of the predefined substance or the predefined environmental condition to undergo a change in absorption spectrum.

8. The system of claim 5, wherein said indicator of at least one of said sensing elements is responsive to presence of the predefined substance or the predefined environmental condition to undergo a change in refractive index.

9. The system of claim 5, wherein said indicator of at least one of said sensing elements is responsive to presence of the predefined substance or the predefined environmental condition to undergo a change in dimensions.

10. The system of claim 5, wherein said indicator of at least one of said sensing elements comprises at least one of the group consisting of: pH sensitive dyes, porphyrins, metalloporphyrins, proteins, anti-bodies and DNA.

11. The system of claim 1, wherein said plurality of sensing elements includes at least three sensing elements.

12. The system of claim 1, wherein said plurality of sensing elements includes at least four sensing elements.

13. The system of claim 1, further comprising a reference element arranged in non-overlapping relation adjacent to said plurality of sensing elements, said reference elements comprising a layered optical element for generating a wavelength-specific interference effect distinct from the wavelength-specific interference effect of each of said sensing elements, said reference element being provided without an indicator so as to provide a calibration reference when illuminated together with said sensing elements.

14. The system of claim 1, wherein said plurality of sensing elements are integrated onto a common semiconductor chip.

15. The system of claim 1, wherein said plurality of sensing elements are mounted in fixed spatial relation to an end of an optical waveguide associated with said illumination arrangement and said spectral analysis arrangement such that said plurality of sensing elements are simultaneously illuminated by illuminating radiation propagating along said optical waveguide and radiation reflected from said sensing elements returns along said optical waveguide.

16. The system of claim 15, wherein said optical waveguide is an optical fiber, and wherein said plurality of sensing elements are attached to a terminal surface of said optical fiber.

17. A method for sensing substances or environmental conditions in a fluid, the method comprising the steps of:
   (a) providing a device comprising a plurality of non-overlapping adjacent sensing elements, each of said sensing elements comprising a layered optical element configured to generate a wavelength-specific interference effect, each of said layered optical elements being configured to be responsive to presence of a predefined substance or a predefined environmental condition to cause an optically detectable change;

(b) employing an illumination arrangement to direct multi-wavelength light simultaneously towards all of said sensing elements;

(c) combining light reflected from or transmitted through said plurality of sensing elements and directing said combined light into a non-imaging spectral analysis subsystem; and (d) employing the spectral analysis subsystem to separate spectral components of light reflected from or transmitted through said sensing elements, to identify spectral features corresponding to the wavelength-specific interference effect of each sensing element, and to detect changes in those spectral features indicative of the presence of the predefined substance or the predefined environmental condition sensed by each sensor element.

* * * * *